United States Patent [19]
Haindl et al.

[11] Patent Number: 5,688,247
[45] Date of Patent: Nov. 18, 1997

[54] PORT CATHETER

[75] Inventors: Hans Haindl, Hauptstr. 39, 30972 Wennigsen; Stephan Langenfeld, Osnabruck, both of Germany

[73] Assignee: Hans Haindl, Wenningsen, Germany

[21] Appl. No.: 356,385

[22] PCT Filed: Jun. 8, 1993

[86] PCT No.: PCT/EP93/01441

§ 371 Date: Dec. 20, 1994

§ 102(e) Date: Dec. 20, 1994

[87] PCT Pub. No.: WO94/00177

PCT Pub. Date: Jan. 6, 1994

[30] Foreign Application Priority Data

Jun. 30, 1992 [DE] Germany ............... 42 21 390.8

[51] Int. Cl.$^6$ ............................................. A61M 5/00
[52] U.S. Cl. ................................. 604/175; 604/174
[58] Field of Search ........................ 604/167, 174, 604/175, 104, 105, 106, 180, 179

[56] References Cited

U.S. PATENT DOCUMENTS

| | | | |
|---|---|---|---|
| 4,986,810 | 1/1991 | Semrad | 604/175 X |
| 5,112,310 | 5/1992 | Grobe | 604/175 |
| 5,122,122 | 6/1992 | Allgood | 604/174 |
| 5,207,644 | 5/1993 | Strecker | 604/175 X |
| 5,217,451 | 6/1993 | Freitas | 604/174 X |
| 5,221,261 | 6/1993 | Termin et al. | 604/175 X |
| 5,232,440 | 8/1993 | Wilk | 604/174 X |
| 5,257,975 | 11/1993 | Foshee | 604/175 X |
| 5,267,960 | 12/1993 | Hayman et al. | 604/174 X |
| 5,273,529 | 12/1993 | Idowu | 604/174 X |
| 5,300,086 | 4/1994 | Gory et al. | 604/175 X |
| 5,413,565 | 5/1995 | Michels et al. | 604/175 X |

FOREIGN PATENT DOCUMENTS 480653  4/1992  European Pat. Off. ......... 604/174

*Primary Examiner*—Sam Rimell
*Attorney, Agent, or Firm*—Banner & Witcoff, Ltd.

[57] ABSTRACT

A port catheter, designed to be implanted by puncturing, has a cylindrical casing (1) in which there is a chamber (22) dosed off on one side by a membrane (4) which can be punctured by an injection needle and connectable on the other side to a catheter (8). Securing loops (9, 10) project from the casing (1) and can be folded together by special means during insertion and unfold when the means are released. The securing loops (9, 10) are made of spring wire surrounding the casing (1) at two separate points. The securing loops (9, 10) are thus relatively stiff in the securing direction but can be bent circumferentially about the casing (1) and held in this position for implantation.

19 Claims, 2 Drawing Sheets

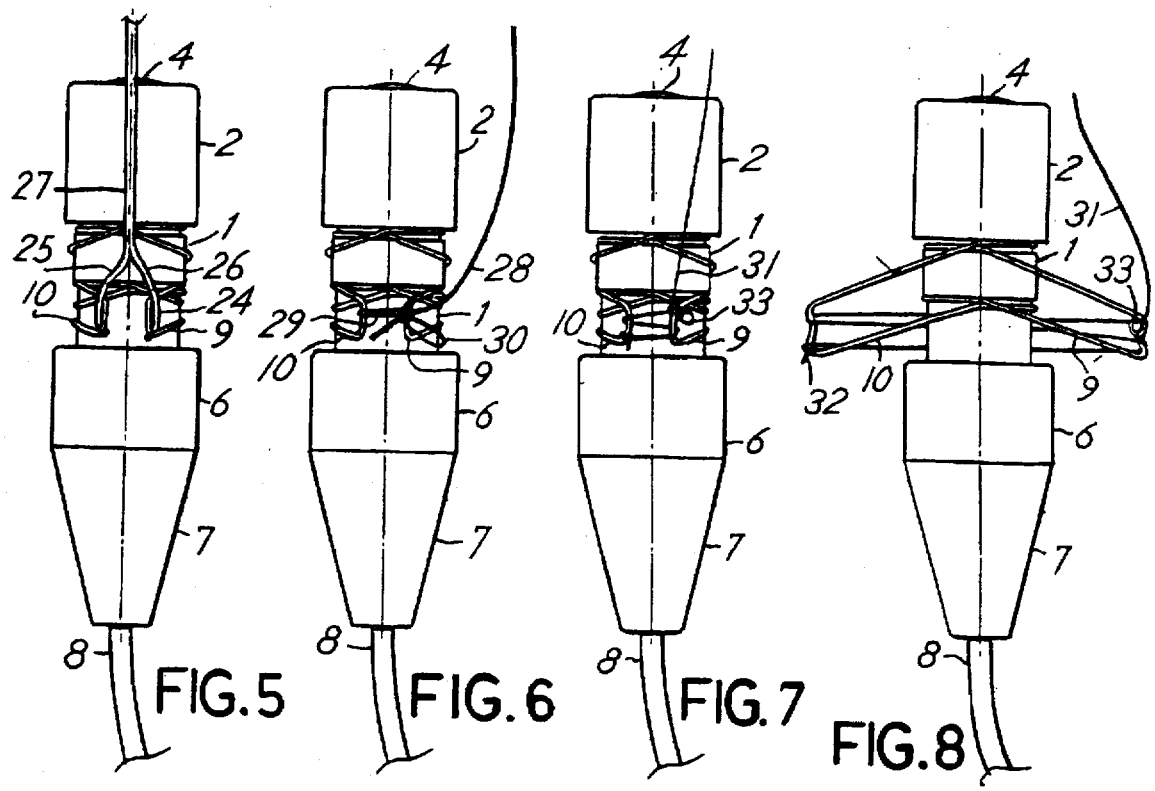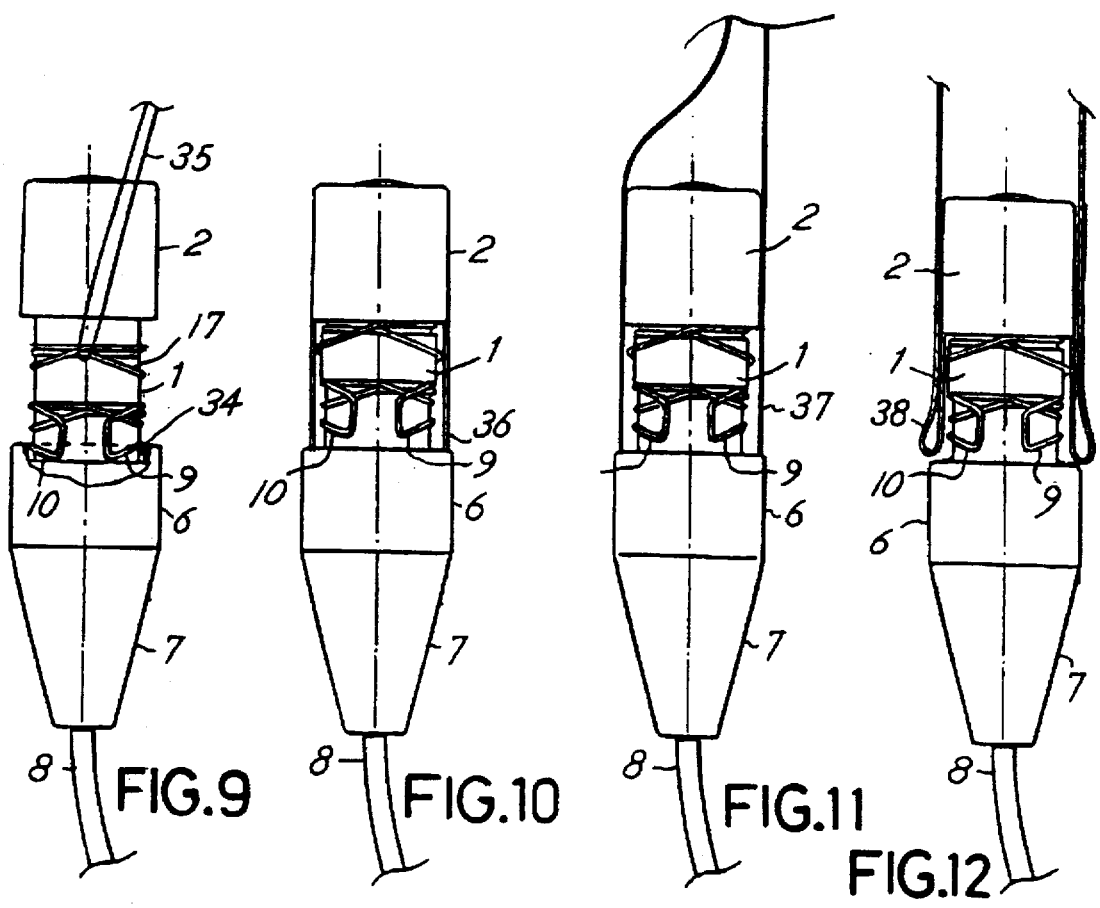

PORT CATHETER

BACKGROUND OF THE INVENTION

The invention pertains to a port catheter having a generally cylindrical casing with a chamber in it, which is sealed on one side by a needle-piercable membrane and to the other side of which is connected a tube catheter.

A port catheter of the referred type is already known from DE 38 37 779 C2. It can be implanted in the patient's body by means of a puncture creating a port of entry to the blood-vessel system or to another body cavity that cannot be reached otherwise. The port catheter resides under the skin after the puncture, and its membrane can be punctured through the skin with a needle. A tube is connected to the casing of the port catheter and takes the medications to their site of activity, where they are needed.

A port catheter of this type is very small to ease its implantation by means of a skin puncture. To be able to anchor the port catheter in spite of its small dimensions in the subcutaneous fat tissue, anchoring loops are fitted on the outer wall of the port catheter body. After the implantation, the introduction sleeve is pulled over the side of the already removed introduction cone. This results in the straightening up of the anchoring or securing loops, which were compressed to the wall of the port catheter body wall during the insertion, and their penetration into the surrounding fat tissue of the patient. This renders a stabilization of the position to the port catheter. The casing is held in its predetermined position during the insertion by a counter holder.

An object of this invention is to construct a port catheter of the mentioned type, by which the anchoring loops are simply built, simple to construct and simply and safely mounted on the casing. Furthermore it must be ensured, that in the implanted position after pulling the introduction sleeve the anchoring loops spread out and grant the port catheter a high degree of anchoring stability.

The basic object of the invention is achieved through the use of anchoring loops that protrude from the wall of the casing of the port catheter and can be bent together, said anchoring loops being made from spring wire which engage the casing over one position, protrude from this position in opposite directions to form two loops and again engage the casing at a second position axially spaced from the first position.

The basic idea of this invention is that the anchoring loops be made of a spring wire, whose ends embrace or engage the casing on two points that are axially apart from each other. This renders a high grade of bending strength diagonally to the longitudinal axis of the port catheter. In the circumferential direction the anchoring loops let themselves bend further, practically as a continuation of their embracing of the casing. This construction combines a high bending resistance that prevents movements in the axial direction, with a good bending capacity in the circumferential direction that does not require extra anchoring stability.

The materials for the cohesion of the anchoring loops can be variously constructed. A functional construction form consists of a fork with two teeth, which hold the ends of the folded loops together. The fork has a handle that reaches over the end of the casing facing the introduction cone. The ends of the teeth are a little bent over another. After the implantation, the rear end of the fork handle is captured and stretched so that the teeth release the anchoring loops that can now expand.

Another embodiment of the means for keeping the anchoring loops bent together is a string, one end of which embraces both ends of the anchoring loops, and which has a loop, releasable by pulling the other end of the string extending beyond the end of the casing facing the insertion cone. This construction form is extremely simple and reasonable.

Another possibility of using a string is, concerning a broader aspect of the invention, that one end of the string is connected to one of the anchoring loops while the other end passes through an eyelet in the other loop and then over the side of the introduction cone facing the casing. By pulling the string, the folded anchoring loops are kept in the folded position during the implantation of the port catheter. When the string is released, the anchoring loops are freed and can anchor the port catheter effectively. This construction form, with only one pulling-string, has the advantage that it can also help in removing the port catheter. For this purpose, the free end of the string is found by puncture of the skin and pulled. This causes the anchoring loops to bend again making an easy retrieval of the port catheter possible. The advantage can be maximized by winding the string a few times over the ends of both anchoring loops before it is passed through the eyelet. Thus a "cork-opener" effect is achieved that creates, even by the application of smaller pull-forces on the string, greater forces for the bending together or spreading apart of the anchoring loops.

By a further modification of the invention, the means for holding together the folded anchoring loops, comprises an axial nut, in which both ends of the anchoring loops in the bent position are engaged. A string, which is connected to one of the bent together loops with which the anchoring loops are connected to the casing 1, is used for the disengagement. By pulling this string, the loops are freed and can spread apart.

Another functional embodiment for the invention is that a cylindrical ring, made of a material that is rapidly destroyed in the body, surrounds the anchoring loops in the bent position. After the ring is destroyed, the anchoring loops are freed.

A tube, which encapsulates both anchoring loops and reaches far enough backwards so that it can be removed after the implantation, can also serve for holding the folded anchoring loops together. By pulling the tube both anchoring loops are freed and spread themselves. The tube can also be divided in two parts in its length to facilitate a separation from casing 1.

An already known introducing sleeve can also serve as means for keeping the anchoring loops bent. It should be moveable over the entire length of the casing covering the folded anchoring loops, and be placed over the end of the casing facing the introduction cone. This introduction sleeve facilitates the manipulation during implantation and permits other functional construction forms for this extension of the invention to be performed.

Another functional embodiment of this invention is that the anchoring loops comprise the legs of a V that is open in the direction of the cone. The advantage here is that when the introduction sleeve is pulled back, both anchoring loops open slowly and the trauma to the surrounding tissues, which is a possibility by a sudden opening of the anchoring loops, is substantially reduced. This applies also for the use of a tube for keeping the anchoring loops bent. A construction containing an introduction sleeve with an elastic part that functions as a friction-lock on the casing is especially practical. This prevents a sudden independent back movement of the introduction sleeve when it is uncontrolled by the introducing physician, which causes a faster opening of the anchoring loops. Such a friction-lock can consist of a tongue, constructed of cuts in the sleeve, which causes friction with the outer walls of the casing or parts of it.

The construction of the tongue allows for a further functional extension or modification, in which the membrane is compressed against the rear end of the casing by an inwards facing collar of a sleeve, while this sleeve has on its inner side a line of repeated hook-formed depressions, which cling to a complementary line of depressions on the outer wall of the casing. By using the sleeve, a safe and sealed fixture of the membrane is guaranteed. At the same time this permits a further extension, in which the tongue has an inwards pointing crimping which clings in one of the hook-formed depressions in the sleeve, and so connects the insertion sleeve with the casing in a rotary form-dosing configuration. This rotary safe connection facilitates the introduction of the port catheter—the subject of this invention. At the same time it is desirable to construct the cone as a squeezing nut for the fixation of the catheter tube. By mounting the catheter-tube the port catheter can be held against the screwing force of the squeezing nut firmly by the insertion sleeve. In this way it is sure that no resistance-building edge exists when the port catheter is implanted.

BRIEF DESCRIPTION OF THE DRAWINGS

The drawing illustrates several construction examples:

FIG. 5 shows a side view of a second possible embodiment of the invention, with a fork for keeping the anchoring loops bent together;

FIG. 6 shows in a similar representation to FIG. 5 a third embodiment of the invention, with a string for keeping the anchoring loops bent together;

FIG. 7 shows in a similar representation to FIG. 5 a fourth embodiment of the invention with a string for keeping the anchoring loops bent together;

FIG. 8 shows the embodiment shown in FIG. 7, with the anchoring loops in the open position;

FIG. 9 shows a fifth embodiment of the invention, with an axial nut for keeping the anchoring loops bent together;

FIG. 10 shows a sixth embodiment of the invention;

FIG. 11 shows a seventh embodiment of the invention; and

FIG. 12 shows an eighth embodiment of the invention.

DETAILED DESCRIPTION OF THE INVENTION

Figure 1:
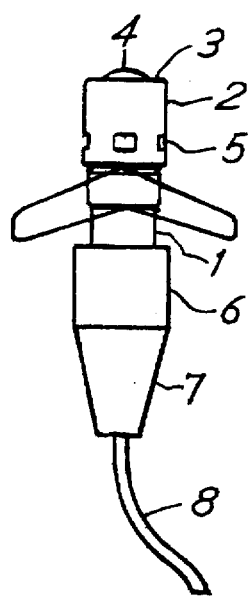
FIG. 1 shows a port catheter of the invention in a side view.

FIG. 1 shows a 1.5 times magnification of a practical construction example of a port catheter. A cylindrical casing 1 has a cap 2 on its end with a collar 3 pointing inwards, which is sealed by pressing a membrane 4 made of silicon-rubber against the rear end of the casing (not seen in FIG. 1). The cap 2 is held onto the casing 1 by hook-formed depressions. At the end of the casing 1 opposite to the membrane 4 there is attached a damping nut 6 with a conical outer shape or cone 7 to facilitate an implantation by puncture. The clamping nut 6 serves for securing a tube catheter 8. Two anchoring loops 9 and 10 are positioned between the cap 2 and the damping nut 6.

Figure 2:
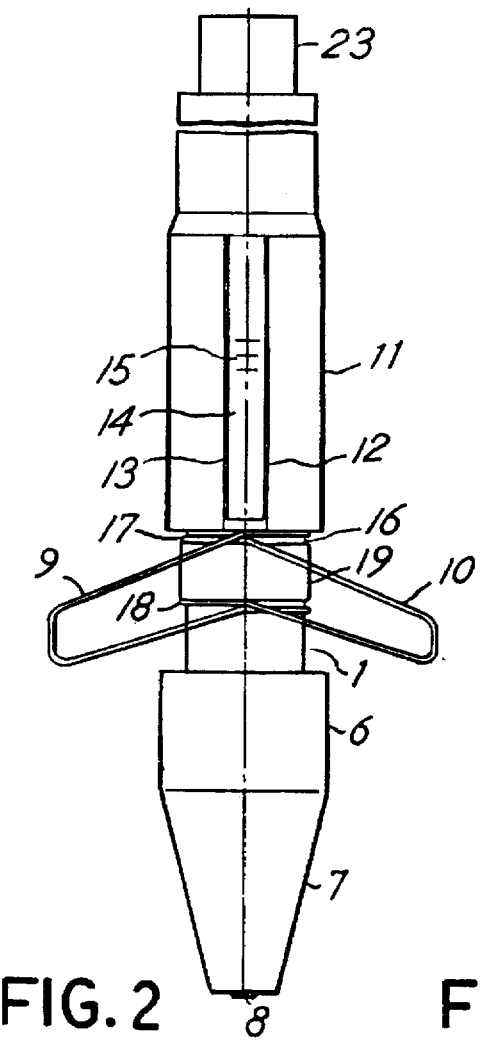
FIG. 2 shows the port catheter of FIG. 1 enlarged, and with a partly mounted insertion sleeve.

FIG. 2 shows the port catheter as in FIG. 1 in a magnified or enlarged view. An insertion sleeve is partially mounted on the end of the casing 1 with the cap 2. The insertion sleeve 11 shows two cuts 12 and 13 that form a tongue containing a crimping or offset 15 that lies in a friction-complementary fashion over the cap 2.

Furthermore FIG. 2 shows that the anchoring loops 9 and 10 in the region of the groove 16 embrace the casing 1 with a loop, 17 and are with this arrangement, safeguarded against axial, as well as radial movements. With a second loop 18, the anchoring loops 9 and 10 embrace the casing 1 on a second, further away position, where they are similarly safeguarded against different kinds of movements. Between the anchoring loops 17 and 18 is seen a thicker part 19 of casing 1. In spite of the safe anchoring of the anchoring loops 9 and 10 to the casing 1 on two axially from another separated points, the anchoring loops 9 and 10 are bent over the casing 1 as anchoring loops 17 and 18 without exceeding their elastical bending zone. In this position it is possible for the insertion sleeve 11 to be moved further on in the direction of the clamping nut 6 over the anchoring loops 9 and 10. This situation is described in FIG. 3. The anchoring loops 17 and 18 are part of the anchoring loops 9 and 10, respectively, and are each secured to the cylindrical casing 1 by being looped thereon and are each on opposite sides of the thicker part of the casing 1 to preclude undesired axial movement of the anchoring loops 9 and 10 on the casing 1.

Figure 3:
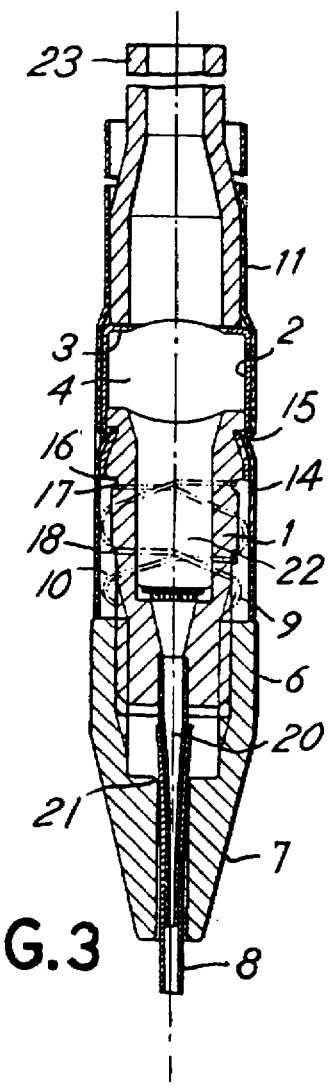
FIG. 3 is a longitudinal section through FIG. 2, with a fully mounted insertion sleeve.

In FIG. 3 we see that the anchoring loops 9 and 10 are in a bent position inside the insertion sleeve. At the same time we see that the crimping 15 of the tongue 14 grasps in the depression 5 of the sleeve 2 by which the insertion sleeve 11 and the casing 1 are or connected in a rotary safe way. This facilitates the screwing of the clamping nut 6 to fasten the cathetertube 8, when it is mounted upon a trumpet like support 20, where it is squeezed with a squeeze-edge 21, to form a connection between the inner space of the catheter 8 and the chamber 22 in the casing 1, into which an injection fluid is injected after the membrane 4 has been pierced by an injection needle.

The rear end of the insertion sleeve is shown shortened in FIGS. 2 and 3. On the inner side of the insertion sleeve 11 we see a small push-rod 23, which helps overcome the counter forces that develop in the casing when the insertion sleeve 11 is pulled back after the implantation.

Figure 4:
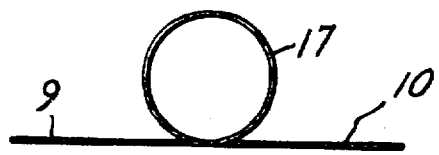
FIG. 4 shows the anchoring loops alone in an axial view.

FIG. 4 shows the anchoring loops 9 and 10 in the same opened position as in FIG. 2, in an axial or transverse view showing the loop 17, behind which is (not visible) the loop 18. Anchoring loops 9 and 10 and anchoring loops 17 and 18 are functionally composed of one endless wire.

FIGS. 5 to 12 demonstrate diverse construction possibilities of the invention in a side view similar to FIG. 1 but with different means for keeping the anchoring loops bent together. Identical parts are marked with numbers corresponding to the numbers mentioned in FIGS. 1 to 3.

The embodiment in FIG. 5 shows the anchoring loops 9 and 10 bent together embracing the casing 1 for the implantation process. They are kept in this position by the teeth 24 and 25 of the fork 26, whose handle 27 protrudes over the end of the casing facing the cone 7 so that the entire fork, with the help of the handle 27 can be dismounted and removed after the implantation. Thus the anchoring loops 9 and 10 are freed and can unfold themselves. The teeth 24 and 25 are a little inwards bent at their ends so that they cannot slide out at the time of the implantation.

The construction example in FIG. 6 shows the anchoring loops 9 and 10 bent together embracing or engaging the casing 1 for the implantation process. They are kept in this position by a string 28 whose one end 29 encircles the anchoring loops 9 and 10, and with the help of a loop 30 holds them together. After the implantation, using the string 28, the anchoring loops are set free. The string 28 reaches over the end of the casing 1 facing the cone 7 so that the string lies outside the patient's body after the implantation and can be grasped.

The embodiment in FIG. 7 shows the anchoring loops 9 and 10 bent together embracing the casing 1 for the implantation process. They are kept in this position by a string 31, which is anchored to point 32 on the anchoring loop 10 and surrounds both anchoring loops 9 and 10 several times. It passes through the eyelet 33 shown on the anchoring loop 9 backwards, over the rear end of casing 1. This construction form has the advantage that the ends of the bent anchoring loops are kept together in a pulley form. Since the string 31 can remain inside the body in a sufficient length, it is possible to find the end of this string by puncturing. Pulling this string causes the anchoring loops 9 and 10 to return to their bent position around the casing 1, thus facilitating the removal of the port catheter. The out spread position of the anchoring loops is shown in FIG. 8, where the eyelet 33 is seen very well.

The construction example in FIG. 9 shows the anchoring loops 9 and 10 bent together embracing the casing 1 for the implantation process. They are kept in this position by an axial groove 34, which is positioned between the squeezing nut 6 and the casing 1, thus securing the anchoring loops from spreading out. A string 35 is placed around the loop 17 which enables the back pulling of loop 17 and with it also loops 9 and 10, thus freeing them from the axial groove 34 and making a spreading out possible.

The construction example in FIG. 10 shows the anchoring loops 9 and 10 bent together embracing the casing 1 for the implantation process. They are kept in this position by a cylindrical ring, made of a material such as polyglycolic acid or gelatine that is destroyed in the body after the implantation thus freeing anchoring loops 9 and 10 and making a spreading out possible.

FIG. 11 shows an embodiment by which the anchoring loops 9 and 10 are bent together and kept in this position by a tube 37, which stretches over the rear end of the port catheter to such a distance that allows its capture after the implantation. By pulling the robe 37 it slides over the anchoring loops 9 and 10 and let them spread out.

The construction form displayed on FIG. 12 is very similar to the form shown in FIG. 11. The difference is that the tube 38 is rolled up in the area of the anchoring loops and it is made of a material that is tearable in the length axis.

While I have shown and described presently preferred embodiments of the invention, it will be apparent that other embodiments may be embraced within the scope of the appended claims.

What is claimed:

1. A port catheter for implantation in a body comprising a casing (1) having a generally cylindrical wall and having a chamber (22) therein, which is sealed on one side by a needle-pierceable membrane (4) and which is connected at (the) an end of the casing opposite from said (on the) membrane (4) with a tube catheter (8), and a cone (7) on the casing (1) that allows the implantation of the port catheter by puncture, and two anchoring loops (9,10) that protrude from the casing wall and can be bent together, the anchoring lops (9,10) comprising a spring wire which embraces the casing (1) over one position, protrudes from this position in two opposing directions taking the form of said two anchoring loops (9,10) and which (meet) meets again to embrace the casing (1), at a second position axially separated from the first position.

2. The port catheter of claim 1, in which both anchoring loops (9,10) are flexible, thus (making) facilitating their bending (in the looping direction possible) around the casing (1) for embracing the casing (1).

3. The port catheter of claim 1, in which (the) there are provided means for (bending) holding together the anchoring loops (9,10) which (consist of) comprises a fork (26) with two teeth (24,25) holding the ends of the (bent together) anchoring loops, the fork (26) (being characterized by a rod (27) or a string) including a post (27) that protrudes beyond the end of the casing (1) facing the cone (7).

4. The port catheter of claim 1, in which the teeth of the fork (24, 25) are bent upon one another.

5. The port catheter of claim 1, in which (the) there are provided means for bending together the anchoring loops (9,10) (consists of) comprising a string (28) having two ends, one end of said string (28) connected to both ends of the bent anchoring loops (9,10) and being held by a (loop) knot, which knot (string) can be released by pulling on its other end (28) which is led out over the end of the casing (1) facing the cone (7).

6. The port catheter of claim 1, in which there are provided means for bending together the anchoring loops (9, 10) which comprise a string (31) having a one end connected to one of the anchoring loops (10) and having another end connected through an eyelet (33) to the other anchoring loop (9) and then is led out over the end of the casing (1) facing the cone (7).

7. The port catheter of claim 1, in which the means for bending together the anchoring loops (9, 10) comprises an axial groove (34) in which both anchoring loops in the bent position are engaged, and a string (35) encircling all loops, including looping area (17, 18) and then is led out over the end of the casing (1) facing the cone (7), said string helping to disengage the anchoring loops from the axial nut.

8. The port catheter of claim 1, in which the means for bending together the anchoring loops (9, 10) comprises a cylindrical ring (36) which encircles the anchoring loops (9, 10) and is constructed of a material that is destroyed in the body after implantation.

9. The port catheter of claim 1, in which the means for bending together the anchoring loops (9, 10) consists of a robe (37, 38) which encompasses the bent together anchoring loops (9, 10) and protrudes beyond the end of the casing (1) facing the cone (7) and can be pulled off from the casing.

10. The port catheter of claim 9, in which the robe is made of a material that is tearable in the longitudinal axis thereof.

11. The port catheter of claim 9, in which the end of the tube encompassing anchoring loops (9, 10) is inwards bent.

12. The port catheter of claim 1, in which the means for bending together the anchoring loops (9, 10) comprises an insertion sleeve, (11) that can be moved over the casing (1) and the anchoring loops (9, 10), and protrudes over the end of the casing (1) facing the cone (7).

13. The port catheter of claim 12, in which both anchoring loops (9, 10), form the legs of a V that is open in the direction of the cone (7).

14. The port catheter of (claims) claim 12 (and 13), in which (an elastic part of) the insertion sleeve (11) includes an elastic part that is friction connected to the casing (1).

15. The port catheter of claim 14, in which the elastic part of the insertion sleeve (11) consists at least of a tongue (14), constructed of cuts (12, 13) in the insertion sleeve (11).

16. The port catheter of claim 15, in which the membrane (4) is connected with an inwards bent metal collar to an end of the casing (1) and the insertion sleeve (11) has on its inner face hook-formed depressions corresponding with complementary depressions on the cylindrical wall of the casing (1).

17. The port catheter of claim 16, in which the tongue (14) has an inwards pointing crimping that engages in the hook-formed depressions on the inner wall of the insertion sleeve (11) and so connects the insertion sleeve (11) with the casing (1).

18. The port catheter of claim 17, which includes a tube catheter and in which the cone (7) is set oft a clamping—nut (6) to facilitate the attaching of (a) the tube catheter.

19. The port catheter of claim 17, in which (the diameter of) the clamping nut (6) has a diameter which is at least equal (identical) to (or slightly bigger than) the diameter of the insertion sleeve (11).

* * * * *